United States Patent

Nakahata

[19]

[11] Patent Number: 5,861,315
[45] Date of Patent: *Jan. 19, 1999

[54] USE OF STEM CELL FACTOR AND SOLUBLE INTERLEUKIN-6 RECEPTOR FOR THE EX VIVO EXPANSION OF HEMATOPOIETIC MULTIPOTENTIAL CELLS

[75] Inventor: Tatsutoshi Nakahata, Tokyo, Japan

[73] Assignees: Amgen Inc.; Tosoh Corporation, both of Thousand Oaks, Calif.

[*] Notice: The term of this patent shall not extend beyond the expiration date of Pat. No. 5,610,056.

[21] Appl. No.: 732,023

[22] Filed: Oct. 16, 1996

Related U.S. Application Data

[63] Continuation of Ser. No. 393,146, Feb. 21, 1995, abandoned, which is a continuation-in-part of Ser. No. 340,559, Nov. 16, 1994, Pat. No. 5,610,056.

[51] Int. Cl.$^6$ ............................. C12N 5/00; A61K 38/20
[52] U.S. Cl. ..................... 435/384; 435/325; 435/347; 435/378; 435/386; 424/93.1; 424/93.7; 424/85.2; 514/2; 514/21

[58] Field of Search ................... 424/93.1, 93.7; 435/325, 347, 378, 384, 386; 514/2, 21

[56] References Cited

PUBLICATIONS

J. Nichols et al. Exp. Cell Res., 1994, vol. 215, pp. 237–239.

K. Yoshida et al. Mechamisms of Development, 1994, vol. 45, pp. 163–171.

M.O. Muench et al. Exp. hematol., 1992, vol. 20, pp. 339–349.

*Primary Examiner*—Ponnathapura Achutamurthy
*Attorney, Agent, or Firm*—Craig A. Crandall; Ron Levy; Steven M. Odre

[57] ABSTRACT

Stem cell factor in combination with soluble interleukin-6 receptor, interleukin-6, for gp130 signaling, supports the proliferation, differentiation and terminal maturation of blood cells from normal human hematopoietic multipotential cells.

8 Claims, 13 Drawing Sheets

FIG. 1

| Factors | No. of Colonies/500 Cells | | | | | |
|---|---|---|---|---|---|---|
| | GM | Blast | Meg | E | Mix | Total |
| | Serum-containing culture | | | | | |
| IL-6 | 6±0.9 | 0 | 0 | 0 | 0 | 6±0.6 |
| sIL-6R | 3±0.5 | 0 | 0 | 0 | 0 | 3±0.7 |
| IL-6+sIL-6R | 13±0.7 | 1±0.7 | 0 | 0 | 0 | 14±1.9 |
| SCF | 13±2.5 | 1±0.7 | 1±0.7 | 0 | 0 | 15±2.1 |
| SCF+IL-6 | 54±4.3 | 10±3.1 | 1±0.6 | 0 | 0 | 65±7.4 |
| SCF-IL-6+sIL-6R | 62±3.7 | 45±7.2 | 13±2.6 | 28±5.8 | 122±22.8 | 270±17 |
| IL-3 | 23±1.8 | 1±0.7 | 0 | 0 | 0 | 24±1.7 |
| IL-3-IL-6+sIL-6R | 29±2.1 | 12±5.0 | 1±0.7 | 30±4.9 | 21±7.1 | 93±7.1 |
| GM-CSF | 51±4.0 | 1±1.0 | 0 | 0 | 0 | 52±10 |
| GM-CSF+IL-6+sIL-6R | 89±6.8 | 8±3.1 | 0 | 0 | 0 | 97±11 |
| G-CSF | 49±3.7 | 1±1.4 | 0 | 0 | 0 | 50±6.6 |
| G-CSF+IL-6+sIL-6R | 61±4.0 | 6±3.4 | 0 | 0 | 0 | 67±7.8 |
| | Serum-free culture | | | | | |
| Il-6 | 0 | 0 | 0 | 0 | 0 | 0 |
| IL-6+sIL-6R | 0 | 0 | 0 | 0 | 0 | 0 |
| sIL-6R | 0 | 0 | 0 | 0 | 0 | 0 |
| SCF | 1±1.7 | 0 | 0 | 0 | 0 | 1±1.7 |
| SCF+IL-6 | 4±0.7 | 0 | 0 | 0 | 0 | 4±2.1 |
| SCF-IL-6+sIL-6R | 5±1.8 | 7±3.3 | 5±2.1 | 8±3.5 | 45±4.3 | 70±5.4 |
| IL-3 | 5±0.7 | 0 | 0 | 0 | 0 | 5±0.7 |
| IL-3+IL-6+sIL-6R | 6±1.9 | 0 | 0 | 0 | 0 | 6±1.9 |
| GM-CSF | 1±0.5 | 0 | 0 | 0 | 0 | 1±0.5 |
| GM-CSF+IL-6+sIL-6R | 3±1.0 | 0 | 0 | 0 | 0 | 3±1.0 |
| G-CSF | 3±0.8 | 0 | 0 | 0 | 0 | 3±0.8 |
| G-CSF+IL-6+sIL-6R | 3±1.4 | 0 | 0 | 0 | 0 | 3±1.4 |

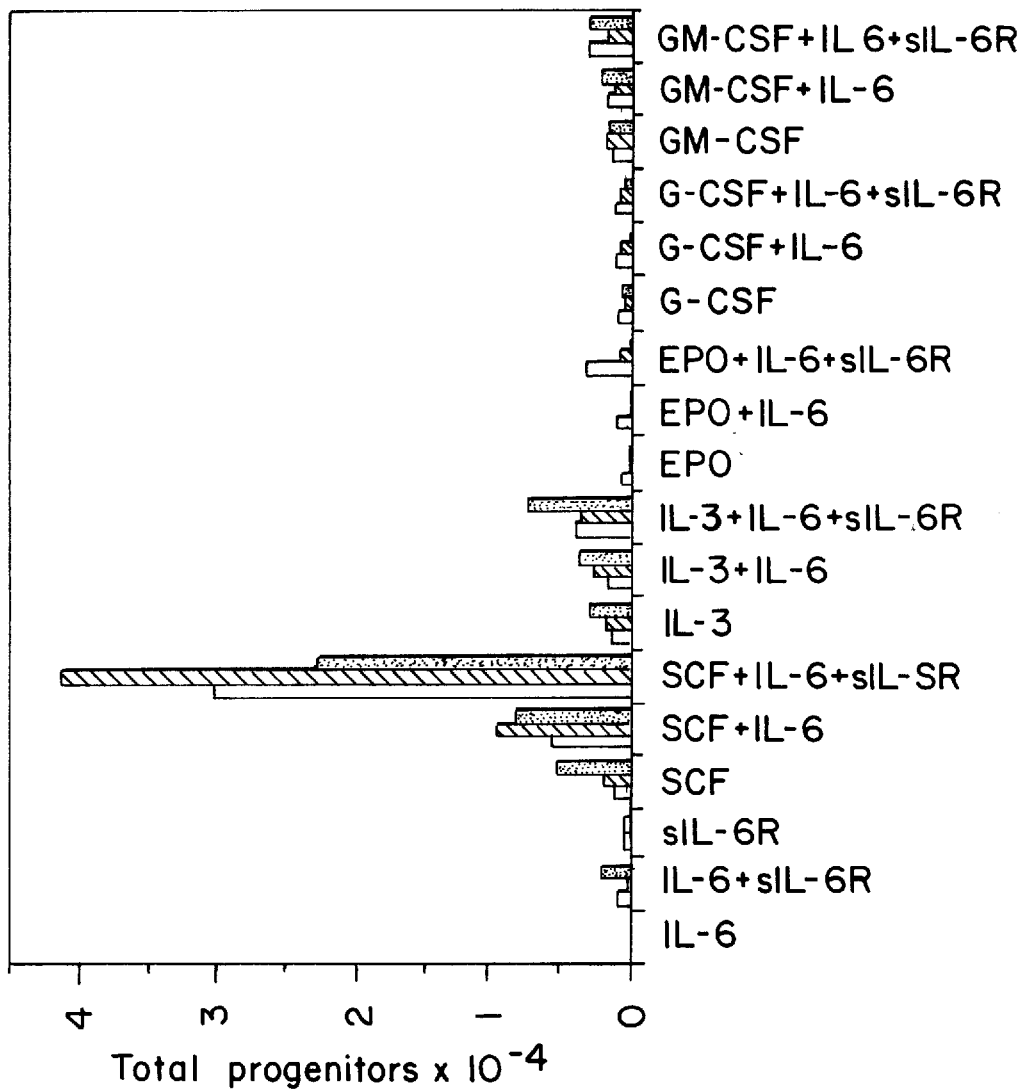

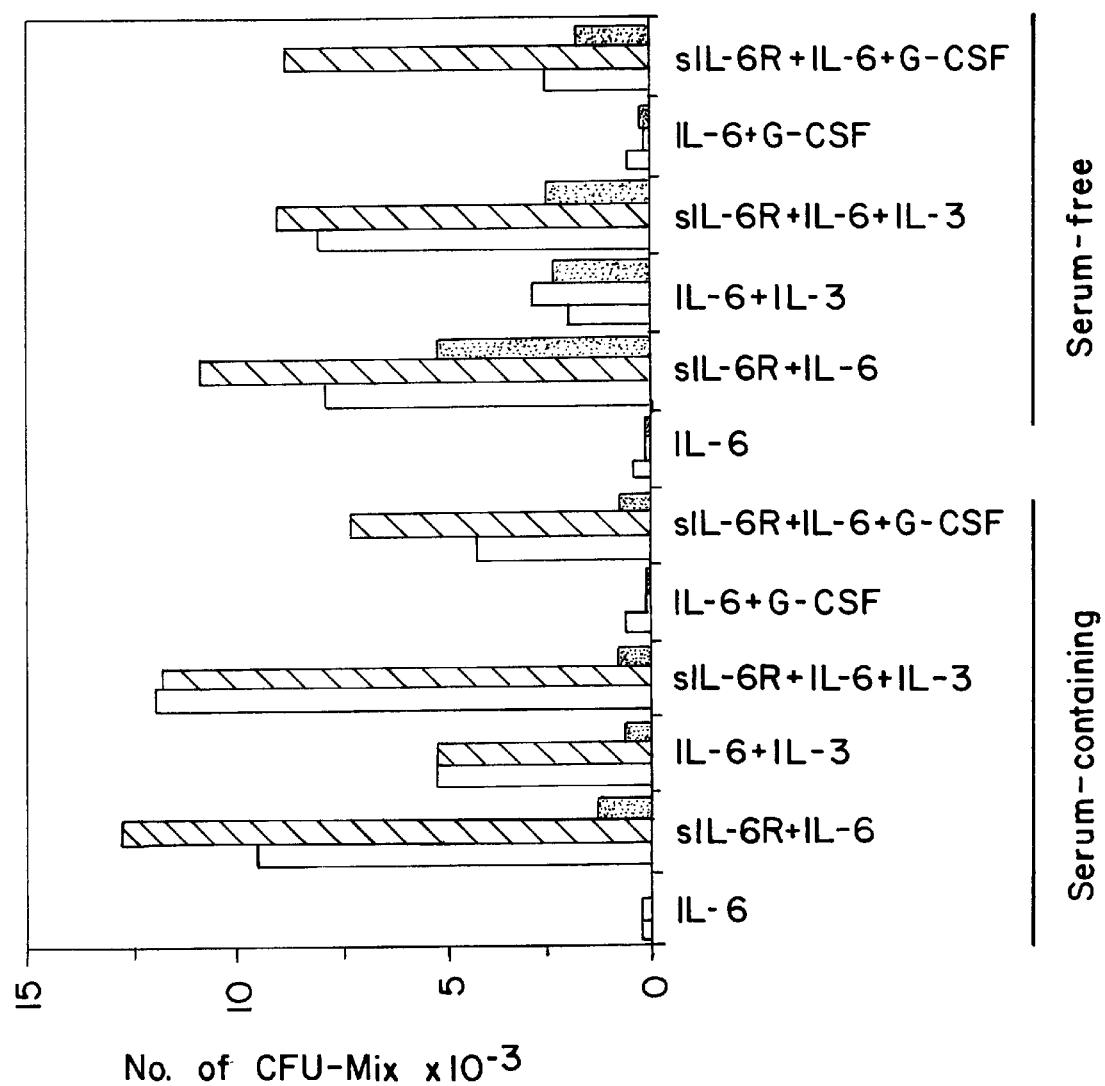

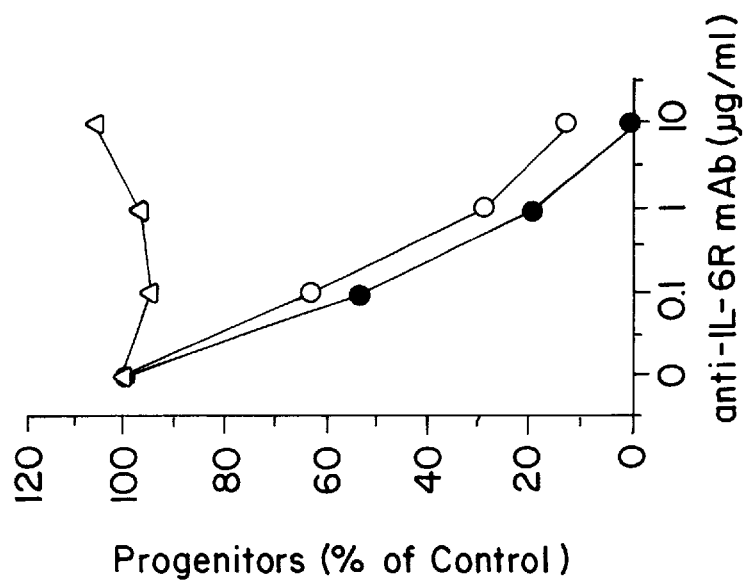
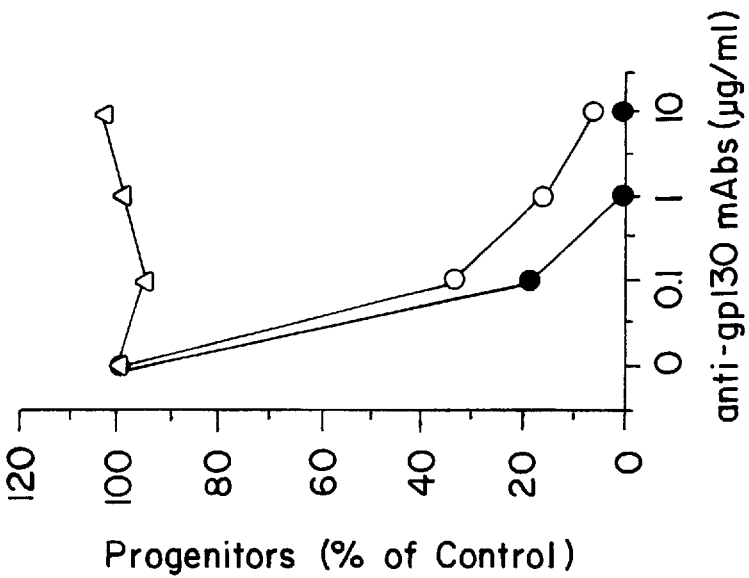

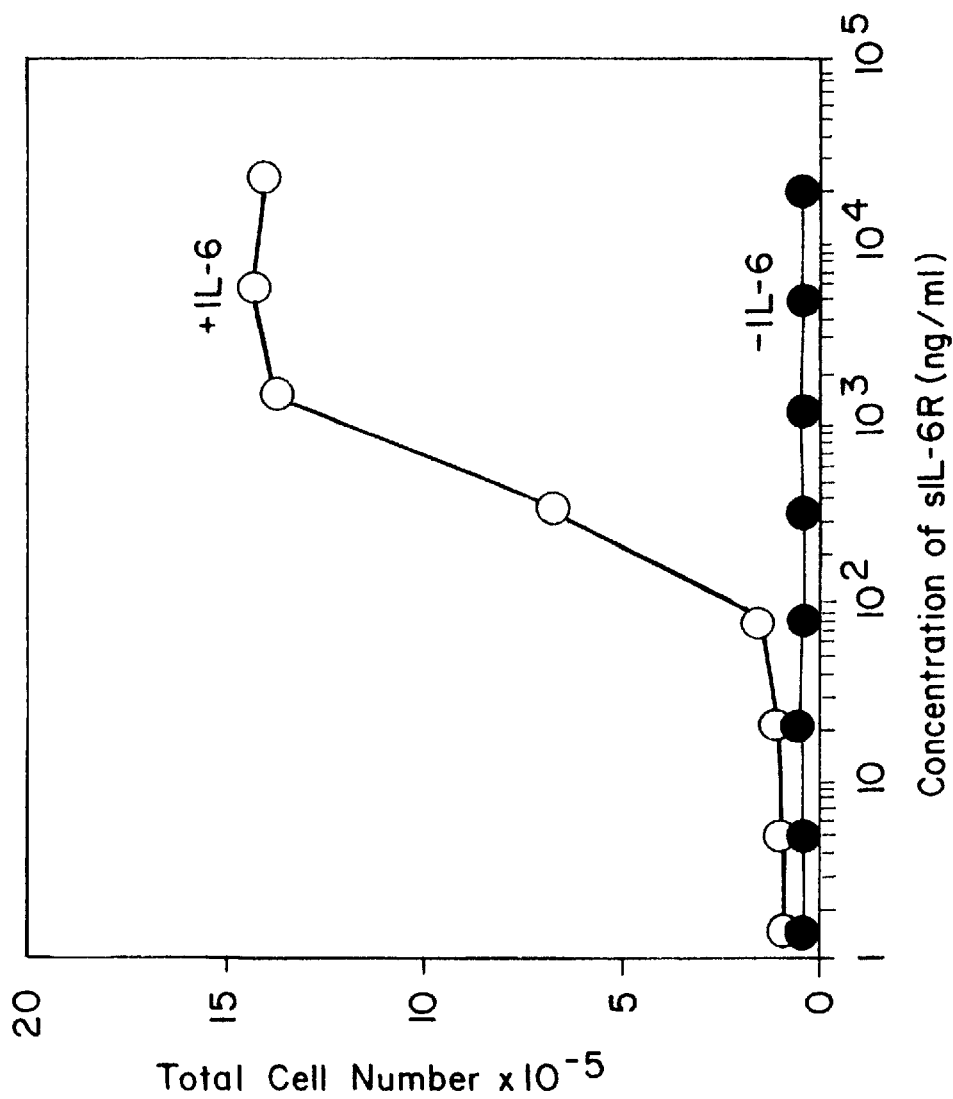

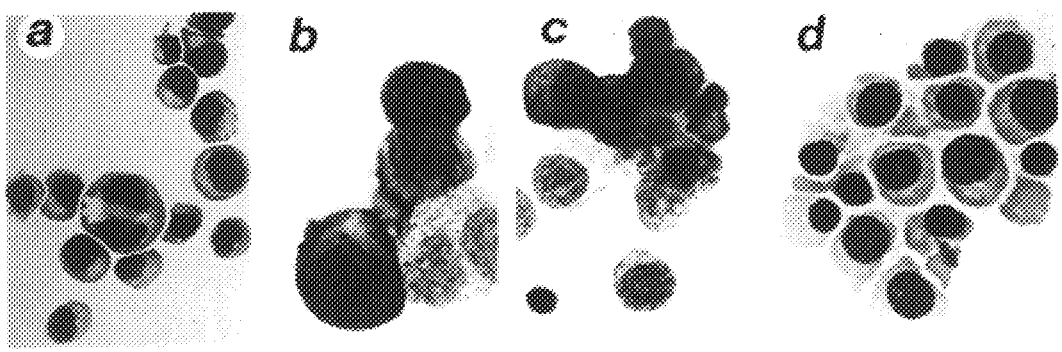
FIG.9A  FIG.9B  FIG.9C  FIG.9D
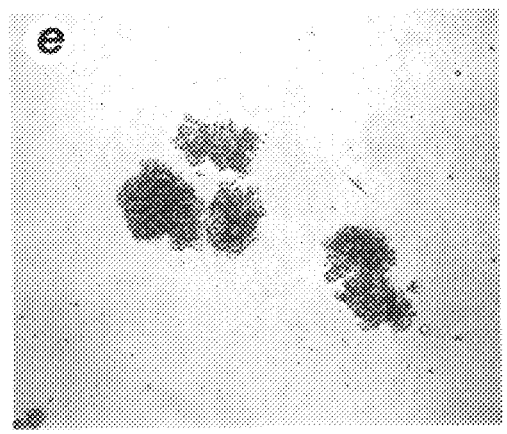
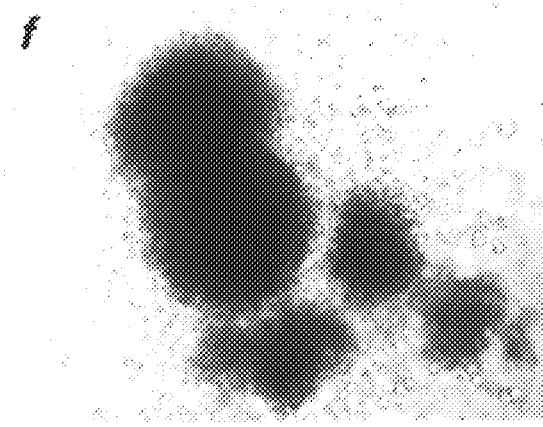
FIG.9E  FIG.9F

FIG.10

| Culture time | Day 7 | | | Day 14 | | | Day 21 | | |
|---|---|---|---|---|---|---|---|---|---|
| Cell number (x10³) | Total cell | E-blast | Erythrocyte | Total cell | E-blast | Erythrocyte | Total cell | E-blast | Erythrocyte |
| Il-6 | 0.9 | 0 | 0 | 0 | 0 | 0 | 0 | 0 | 0 |
| sIL-6R | 0.6 | 0 | 0 | 0 | 0 | 0 | 0 | 0 | 0 |
| IL-6+sIL-6r | 1.9 | 0 | 0 | 0 | 0 | 0 | 0 | 0 | 0 |
| SCF | 5.5 | 0 | 0 | 1.7 | 0 | 0 | 4.4 | 0 | 0 |
| SCF+IL-6 | 11.7 | 0 | 0 | 43.8 | 0 | 0 | 15.0 | 0 | 0 |
| SCF-IL-6+sIL-6R | 75.8 | 28.7 | 0 | 1062.0 | 640.0 | 201.8 | 4346.0 | 2859.6 | 126.1 |
| EPO | 16.6 | 16.6 | 0 | 215.0 | 200.2 | 14.9 | 18.8 | 11.8 | 7.0 |
| EPO+IL6 | 16.6 | 16.6 | 0 | 230.0 | 212.1 | 17.9 | 20.0 | 9.2 | 10.8 |
| EPO+IL-6+sIL-6R | 19.7 | 19.2 | 0 | 230.0 | 220.1 | 9.9 | 56.3 | 53.8 | 1.8 |
| IL-3 | 5.0 | 0 | 0 | 18.1 | 0 | 0 | 3.8 | 0 | 0 |
| IL-3+IL-6 | 7.5 | 0 | 0 | 16.9 | 0 | 0 | 25.0 | 0 | 0 |
| IL-3+IL-6+sIL-6R | 10.0 | 0 | 0 | 50.0 | 23.2 | 0 | 50.0 | 25.3 | 0 |
| G-CSF | 2.5 | 0 | 0 | 4.4 | 0 | 0 | 5.0 | 0 | 0 |
| G+IL-6 | 2.2 | 0 | 0 | 5.6 | 0 | 0 | 5.0 | 0 | 0 |
| G+IL-6+sIL-6R | 2.2 | 0 | 0 | 3.1 | 0 | 0 | 1.3 | 0 | 0 |
| GM-CSF | 1.6 | 0 | 0 | 0.6 | 0 | 0 | 2.5 | 0 | 0 |
| GM+IL-6 | 1.6 | 0 | 0 | 3.8 | 0 | 0 | 3.8 | 0 | 0 |
| GM+IL-6+sIL-6R | 4.1 | 0.1 | 0 | 3.1 | 0.2 | 0 | 7.5 | 1 | 0 |

USE OF STEM CELL FACTOR AND SOLUBLE INTERLEUKIN-6 RECEPTOR FOR THE EX VIVO EXPANSION OF HEMATOPOIETIC MULTIPOTENTIAL CELLS

This application is a continuation of application Ser. No. 08/393,146 filed Feb. 21, 1995 abandoned, which is a continuation-in-part of application Ser. No. 08/340,559, filed Nov. 16, 1994, now U.S. Pat. No. 5,610,056 which are hereby incorporated by reference.

BACKGROUND OF THE INVENTION

The present invention relates to the combined use of interleukin-6, soluble interleukin-6 receptor and stem cell factor in cell expansion. In particular, the invention relates to the combined use of these factors in the ex vivo expansion of hematopoietic progenitor/stem cells.

FIELD OF THE INVENTION

The receptor system for interleukin-6 (IL-6) comprises two functionally different chains: a ligand-binding chain (IL-6R) and a non-ligand-binding but signal-transducing chain (gp130). The gp130 chain associates with the IL-6R/IL-6 complex, resulting in the formation of high-affinity IL-6 binding sites and signal transduction (1–4). An extracellular, soluble form of the interleukin-6 receptor (sIL-6R) has been shown to mediate the IL-6 signal through membrane-anchored gp130. A complex of sIL-6R and IL-6 (sIL-6R/IL-6) can associate with gp130 which is expressed on both IL-6R-negative and IL-6R-positive cells. This association induces the homodimerization of gp130 and the activation of the JAK-STAT pathway thereby leading to cellular response (4–8).

IL-6 has been shown to act synergistically with IL-3 and stem cell factor (3CF) to augment the proliferation of human hematopoietic progenitor cells and to support colony formation from dormant murine hematopoietic progenitors (9–11). Little is known, however, about the role of the gp130 signaling pathway in human hematopoiesis.

There has recently been a great deal of interest in the ex vivo expansion of hematopoietic progenitor cells for a variety of clinical uses including gene therapy, the augmentation of bone marrow transplantation (BMT) and the replacement of BMT. Although there are previous reports on the expansion of cell numbers using various combinations of cytokines or stromal cells, the magnitude of expanded progenitor cells that has been achieved, especially multipotential progenitors, is typically low. This suggests that the differentiation and depletion of primitive cells occurs in the expansion cultures (12–15). A recent study has demonstrated that a combination of IL-6 and sIL-6R sustains self-renewal of the pluripotential embryonic stem (ES) cell through the activation of the gp130 signaling process (16).

The purification, cloning and use of IL-6 is known (EP 220 574, published May 6, 1987, Revel et al.; WO 88/00206, published Jan. 14, 1988, Clark et al.) The purification and cloning of sIL-6R has also been reported, as has its combined use with IL-6 in conditions such as bacterial infections, burns and trauma (EP 413 908, published Feb. 27, 1991, Novick et al.; JP 89271865; Yamasaki et al., Science, 241:825–828, 1988). SCF is an early acting hematopoietic factor. The purification, cloning and use of SCF have been reported (see PCT WO 91/05795, entitled "Stem Cell Factor"). The use of SCF has been described for enhancing the engraftment of bone marrow and bone marrow recovery as well as for the treatment of leukopenia and thrombocytopenia. The use of SCF in combination with IL-6 has been described, but there are no previous reports on the combined use of SCF, IL-6 and sIL-6R for the expansion of hematopoietic progenitor cells.

SUMMARY OF THE INVENTION

The present invention demonstrates that the combination of soluble IL-6 receptor (sIL-6R) and IL-6 together with stem cell factor (SCF) can support the ex vivo expansion of human hematopoietic multipotential cells. Neither sIL-6R or IL-6, when singly combined with SCF, demonstrates this effect.

The multipotential cells may obtained from cord blood, peripheral blood or bone marrow. The multipotential hematopoietic cells may include progenitor and/or stem cells obtained by CD34 selection or stem cells functionally selected by the removal of proliferating cells.

The cytokines may be provided as a kit which includes individual containers of the separate cytokines, or one or more of the cytokines might be provided as a mixture in a single container.

In addition, the present combination of cytokines can support the proliferation, differentiation and terminal maturation of erythroid cells from purified human hematopoietic stem cells in the absence of erythropoietin (EPO). Neither sIL-6R or IL-6, when singly combined with SCF, demonstrates this effect in the absence of erythropoietin.

The studies demonstrate the generation of erythroid cells from hematopoietic stem cells (e.g., CD34$^+$ cells) by means of a combination of sIL-6R, IL-6 and SCF. The effectiveness of the cytokines was also confirmed in serum-free cultures. A number of erythroid bursts and mixed erythroid colonies, containing a large number of mature erythroid cells, were developed from CD34$^+$ cells in methylcellulose culture with the combination of sIL-6R, IL-6 and SCF. The addition of anti-gp130 monoclonal antibodies to the cultures completely abrogated the production of erythroid cells, whereas the addition of anti-erythropoietin antibody failed to affect the generation of erythroid cells from CD34$^+$ cells.

The results demonstrated that mature erythroid cells can be produced from hematopoietic progenitors in the absence of erythropoietin. Together with previous reports that human sera contain detectable levels of sIL-6R, IL-6 and SCF (26–28), it is likely that normal erythropoiesis is regulated physiologically by two different pathways: erythropoietin-mediated signaling and a novel mechanism with gp130 in combination with SCF signaling.

BRIEF DESCRIPTION OF THE DRAWINGS

FIG. 1 depicts the colony formation results from mulitpotential cells cultured in the presence of designated factor combinations.

FIG. 3 depicts the expansion of progenitor cells supplemented with the identified factors or combinations of factors at day 7 (open bars), day 14 (oblique bars) and day 21 (filled bars).

FIG. 4 depicts the expansion of progenitor cells in both serum-containing and serum-free cultures supplemented with various factor combinations in the presence of SCF at day 7 (open bars), day 14 (oblique bars) and day 21 (filled bars).

FIG. 5 depicts the effects of varying concentrations of anti-human gp130 monoclonal antibodies (A) and anti-human IL-6R monoclonal antibody (B) on the expansion of total progenitor cells (o) and CFU-Mix (•).

FIG. 6 illustrates the effects of varying amounts of sIL-6R in the presence of IL-6 and SCF.

FIG. 9 depicts the nature of the generated erythroid cells.

FIG. 10 illustrates the total cell numbers, E-blasts and erythrocytes produced by different combinations of cytokines at 7, 14 and 21 days of culture. IL-3 is interleukin-3, G-CSF is granulocyte colony stimulating factor, and GM-CSF is granulocyte-macrophage colony stimulating factor.

DETAILED DESCRIPTION OF THE INVENTION

Figure 2B:
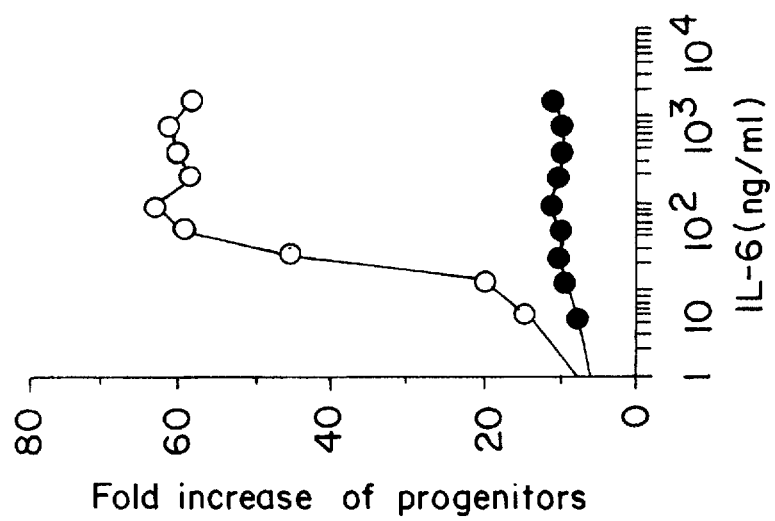
FIG. 2 depicts the expansion of progenitor cells at varying concentrations of sIL-6R in the presence (○) or absence (•) of IL-6, as well as the expansion of progenitor cells at varying concentrations of IL-6 in the presence (○) or absence (•) of sIL-6R

The present invention results from the investigation of the potential role of gp130 signaling, which can be initiated by the activity of the complex of sIL-6R and IL-6 on human hematopoietic stem/progenitor cells. The results presented herein indicate that gp130 signaling involving sIL-6R and IL-6, in the presence of SCF, dramatically stimulates the ex vivo expansion of human primitive hematopoietic progenitor cells.

gp130, a signal transducing receptor component of IL-6, associates with a complex of IL-6 ligand and IL-6 receptor (IL-6R) and transduces signals. To examine the role of gp130 signaling in the expansion of human hematopoietic progenitor cells, the effects of a recombinant soluble human IL-6 receptor (sIL-6R) and/or IL-6 were tested in combination with various cytokines on CD34$^+$ cells.

A combination of sIL-6R and IL-6 (sIL-6R/IL-6) was found to dramatically stimulate the expansion of hematopoietic progenitor/stem cells as well as CD34$^+$ cells in the presence of stem cell factor (SCF). Neither the combination of sIL-6R and SCF nor the combination of IL-6, and SCF provided this result. A significant generation of multipotential hematopoietic progenitors occurred over a period of three weeks in suspension cultures receiving sIL-6R/IL-6/SCF. The efficient formation of colonies, especially multilineage and blast cell colonies, was observed in both serum-containing and serum-free cultures supplemented with the combined cytokines. The initial hematopoietic progenitor/stem cells may be obtained from any suitable cell source including the fetus, placenta, cord blood, peripheral blood, or bone marrow. These multipotential hematopoietic cells may include progenitor and/or stem cells obtained by CD34 selection. Optionally, the multipotential hematopoietic cells may be stem cells which are functionally selected or isolated by the removal of proliferating cells (Berardi et al., *Science*, 267:104–108, 1995).

The present invention demonstrated that two signal pathways, gp130 signaling and c-Kit signaling which are initiated by sIL-6R/IL-6 and SCF, respectively, synergistically promote the ex vivo expansion of human hematopoietic progenitor cells. sIL-6R has been reported to potentiate agonistic effects in the presence of IL-6 on some cell lines such as BAF-m130 cells, gp130 cDNA-transfected cells, and the murine osteoclasts (6–8,25). The present findings, however, demonstrated that sIL-6R/IL-6 in the presence SCF is a very potent stimulator for the proliferation of human primitive hematopoietic progenitors. Previous reports on ex vivo expansion have failed to demonstrate such a striking synergy as found with the sIL-6R/IL-6/SCF combination for the stimulation of human primitive hematopoietic cells.

In vitro expansion of hematopoietic progenitor cells is an attractive means of preparing hematopoietic cells suitable for potential clinical application including gene therapy and cell replacement. Various combinations of cytokines have been reported to be useful in the expansion of progenitor cells (12–15). SCF, IL-3 and IL-6 are generally accepted as the cytokines having the greatest affect on primitive hematopoietic cells, and the combination of these factors has been widely used as the basic and most potent set of cytokines for the expansion of hematopoietic progenitor cells. The present invention, however, demonstrates that the combination of sIL-6R with IL-6 and SCF (sIL-6R/IL-6/SCF) is superior in terms of the expansion rate of primitive progenitor cells, including CFU-Mix or CFU-Blast.

Previous studies have been based on culturing CD34$^+$ cells from human peripheral blood in the presence of a combination of IL-3, IL-6 and SCF with some other cytokine(s), such as G-CSF, GM-CSF, IL-1 or EPO. Such studies show that the combinations may be useful for the generation of progenitors in serum-containing suspension culture (12,13). While an approximately 60-fold increase of CFU-GM was previously achieved with IL-3 combinations, however, CFU-Mix was not expanded and no CFU-Mix or BFU-E were detected at day 14 of culture. Such a finding suggests that relatively late stage progenitors were predominantly expanded in these cultures. In contrast, the efficient expansion of multipotential hematopoietic progenitors in suspension culture and the dramatic formation of Mix and Blast colonies in methylcellulose culture, using the present invention, indicate that sIL-6R/IL-6 stimulates an earlier stage of primitive hematopoietic cells or even pluripotent stem cells.

The addition of anti-gp130 monoclonal antibody (mAb) or anti-IL-6R mAb to the above cultures was found to dose-dependently inhibit the expansion of progenitor cells in suspension culture. The antibodies also completely blocked the formation of multilineage colonies in methylcellulose culture. This finding clearly demonstrated that the observed effects of sIL-6R/IL-6 were provided through the interaction of the IL-6-bound sIL-6R molecule to a membrane-anchored gp130 on the target cells.

Recent studies have shown that gp130 was ubiquitously expressed on cells, and that the self-renewal of ES cells can be maintained by the sIL-6R/IL-6 complex without LIF in vitro (6,16,18). Information remains incomplete, however, on which cytokine receptors are normally expressed on human CD34$^+$ hematopoietic stem/progenitor cells. Certainly, c-Kit receptors for SCF are present and, in our studies, gp130 appears to be present in all CD34$^+$ cells, while IL-6R appears to be present in only a small population of CD34$^+$ cells, as determined by immunostaining. A complex of sIL-6R/IL-6 may enhance the IL-6 signal in IL-6R-positive cells and, more importantly, may mediate the signal via gp130 in IL-6R-negative CD34$^+$ cells which are normally unresponsive to IL-6. Because sIL-6R/IL-6 functions only in the presence of SCF, as revealed in the present study, the coexpression of gp130 and c-Kit on progenitor cells and the coactivation of these signal pathways leads to a dramatic proliferation of human hematopoietic progenitor cells for potential clinical applications.

EXAMPLES

Example 1

Effect of sIL-6R, IL-6 and SCF on Colony Formation from CD34+ Cells in Methylcellulose Culture

MATERIALS AND METHODS

Cell Preparation. Human umbilical cord blood was obtained during normal, full-term deliveries and was collected according to institutional guidance. Mononuclear cells (MNC) were separated by Ficoll-Hypaque density gradient centrifugation after depletion of phagocytes with Silica (IBL, Fujioka, Japan). CD34+ cells were purified from MNC using magnetic beads bearing anti-CD34 antibody (Dynabeads M-450 CD34; Dynal, Oslo, Norway) to bind the CD34+ cells, a Dynal Magnetic Particle Concentrator to separate the cells from MNC, and DETACHaBead CD34 (Dynal) to separate the selected cells from the beads. The selection and separation processes were performed in accordance with the manufacturer's instructions. Eighty-five to ninety-five percent of the cells separated were confirmed as CD34 positive by FACS analysis (Ortho Diagnostics Systems, Westwood, Mass.).

Receptor and Cytokines. The cloning, expression and purification of recombinant human IL-6 and sIL-6R are well characterized as previously described (17,18). Human SCF (Amgen; Thousand Oaks, Calif.), human IL-3, granulocyte-macrophage colony-stimulating factor (GM-CSF) and erythropoietin (EPO) (Kirin Brewery Co. Ltd.; Tokyo, Japan), and human granulocyte colony-stimulating factor (G-CSF) (Chugai Pharmaceutical Co.; Tokyo, Japan) were used to evaluate the affects of a variety of cytokine combinations on the cells. All of the cytokines were pure recombinant molecules and were used at concentrations to induce an optimal response in the methylcellulose cultures of human hematopoietic cells. These concentrations are 100 ng/ml of SCF, 200 U/ml of IL-3, 2 U/ml of EPO, and 10 ng/ml of G-CSF and GM-CSF.

Suspension Culture. Purified CD34+ cells were incubated in a suspension culture using known techniques (21,22). The culture mixtures contained 2000 CD34+ cells, α-medium (ICN Flow; ICN BIOMEDICALS, Inc., Costa Mesa, Calif.), 20% fetal bovine serum (FBS; HyClone, Utah), 1% crystallized and deionized fraction V bovine serum albumin (BSA, Sigma) and the different combinations of cytokines. One milliliter of the culture mixture was incubated in each well of a 24-well tissue plate (Nunc, Kamstrup, Denmark) at 37° C. in a humidified atmosphere flushed with 5% $CO_2$, 5% $O_2$ and 90% $N_2$. Serum-free suspension culture consisted of 2% pure BSA (Sigma), 10 μg/ml insulin, 200 μg/ml transferrin (Sigma), $10^{-5}$M mercaptoethanol (Eastman) and 40 μg/ml low-density lipoprotein (Sigma), instead of FBS and BSA (22).

At weekly intervals, the cultures were depopulated by the removal of one-half the culture volume, which volume was then replaced with newly-prepared medium containing the same combination of cytokines. Cells in the collected medium were washed and counted (12–15). The total number of hematopoietic progenitor cells generated at each time point in the culture were evaluated by further culturing a fraction of the expanded cells in a clonal methylcellulose assay. For the blocking studies of Example 3, anti-gp130 mAb or anti-IL-6R mAb was added at the beginning of culture.

Clonal Culture. The inoculated CD34+ cells and their progenies in the suspension culture were incubated in triplicate at concentrations of 500 cells/ml for CD34+ cells and $2 \times 10^3$ to $10 \times 10^3$ cells/ml for cultured cells in methylcellulose culture (23). Culture mixtures contained the cells, α-medium, 0.9% methylcellulose (Shinetsu Chemical Co., Tokyo, Japan), 30% FBS, 1% BSA, $5 \times 10^{-5}$M mercaptoethanol and various combinations of cytokines with or without sIL-6R. One milliliter of cell-containing culture mixture was plated in each 35 mm Lux standard nontissue culture dish and was incubated at 37° C. in a humidified atmosphere flushed with 5% $CO_2$ in air. Serum-free methylcellulose culture contained components identical to those in the serum-containing culture with the exception that 1% pure-BSA, 300 μg/ml human transferrin, 160 μg/ml of soybean lecithin (Sigma) and 96 μg/ml of cholesterol (Nacalai Tesque Inc., Kyoto, Japan) replaced BSA and FBS (11).

A combination of SCF, IL-3, IL-6, EPO and G-CSF was used to determine the various progenitors generated in suspension culture at each time point. All cultures were done in triplicate and scored at day 14 according to known criteria (10,11,23).

RESULTS

FIG. 1 depicts the results from mulitpotential cells cultured in the presence of designated factor combinations. Colonies were scored on day 14. The number of colonies indicate mean ±S.D. of triplicate cultures. (Abbreviations used for the colony types are as follows: GM, granulocyte-macrophage colonies; Meg, megakaryocyte colonies; B, erythroid bursts; Blast, blast cell colonies; Mix, mixed hematopoietic colonies; and GEMM, granulocyte-erythrocyte-macrophage-megakaryocyte colonies) Each of the various cytokines was used in combination with 1280 ng/ml of sIL-6R, 50 ng/ml of IL-6 and/or 100 ng/ml of SCF.

In serum-containing culture, sIL-6R, IL-6, sIL-6R/IL-6 or SCF alone induced only a small number of colonies. A combination of IL-6 and SCF enhanced the formation of GM and Blast colonies compared with IL-6 or SCF supplement alone. The most striking generation of colonies was observed in the culture supplemented with sIL-6R, IL-6 and SCF as a plating efficiency as high as over 50%. The addition of sIL-6R to the combination of IL-6 and SCF increased total colony numbers 4.2-fold. The number of colonies induced by sIL-6R/IL-6/SCF was 11.3-fold greater than that using IL-3, 5.2-fold greater than that using GM-CSF, and 5.4-fold greater than that using G-CSF. Considerable numbers of Blast colonies and Mix colonies with large size, most of which were GEMM, were developed in addition to a number of Meg colonies and erythroid bursts in the sIL-6R/IL-6/SCF supplemented culture. More than 60% of the colonies induced by sIL-6R/IL-6/SCF were GEMM and Blast colonies, whereas most of the colonies induced by IL-3, GM-CSF and G-CSF were GM colonies.

To exclude the possible influence of some unknown factor(s) in the FBS, a serum-free culture was also performed. The most significant colony formation was again observed in the cultures supplemented with sIL-6R/IL-6/SCF. The addition of sIL-6R to the combination of IL-6 and SCF increased total colony numbers 17.5-fold. The combination also stimulated the formation of a large number of Mix and Blast colonies, in addition to Meg colonies and erythroid bursts. No colonies or only a few GM colonies developed in the other factor combinations.

When sIL-6R/IL-6 was tested in combination with other factors as shown in FIG. 1, a slight synergy between sIL-6R/IL-6 and either IL-3, GM-CSF or G-CSF was observed in serum-containing cultures. No synergy was found between sIL-6R/IL-6 and those factors, however, in serum-free culture. This result indicates that sIL-6R/IL-6 specifically synergizes with SCF for the proliferation of CD34$^+$ progenitor cells.

Example 2

Figure 2A:
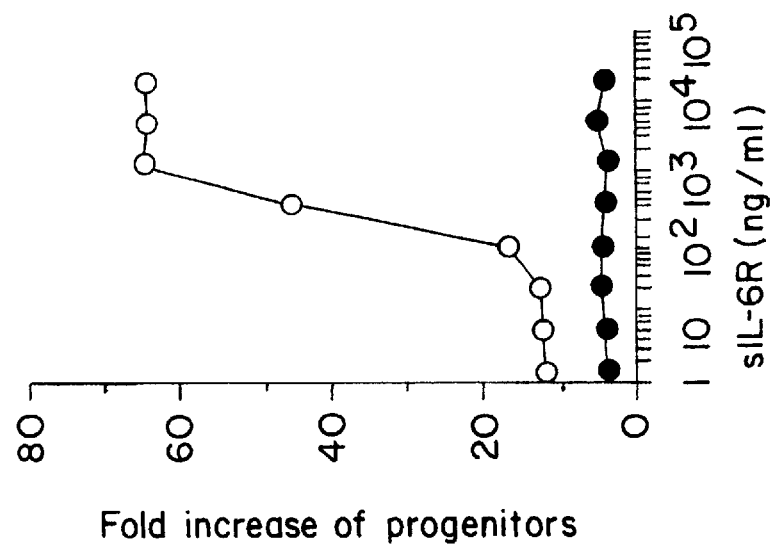

Effect of sIL-6R, IL-6 and SCF on Expansion of Hematopoietic Multipotential Cells in Suspension Culture Studies were performed using serum-containing suspension cultures of CD34$^+$ cells in the presence of varying concentrations of sIL-6R in combination with SCF alone or an IL-6/SCF combination. Progenitors derived from the cultures were assayed after 14 days of incubation. FIG. 2 illustrates the progenitor cell expansion results, after 14 days in serum-containing suspension culture, using the sIL-6R/IL-6/SCF combination on 2000 human CD34$^+$ cells containing 840 progenitors (SCF 100 ng/ml). FIG. 2A depicts the increase of progenitor cells at varying concentrations of sIL-6R in the presence (○) or absence (•) of IL-6 (50 ng/ml). FIG. 2B depicts the increase of progenitor cells at varying concentrations of IL-6 in the presence (○) or absence (•) of sIL-6R (1280 ng/ml). As shown in FIG. 1A, the total of progenitors dramatically increased in accordance with the concentration of sIL-6R. This increase was detectable using sIL-6R at a concentration of as low as 80 ng/ml. The increase plateaus at an approximately 70-fold increase of progenitors using sIL-6R at a concentration of 1280 ng/ml.

In the absence of IL-6, however, sIL-6R failed to expand the total progenitor cells. The optimal expansion of progenitors also appeared to depend on the concentration of IL-6. The maximal increase of progenitor cells (a 63-fold increase) was obtained using IL-6 concentrations exceeding 50 ng/ml in the presence of sIL-6R (FIG. 2B). In contrast, in the absence of sIL-6R, only about a 10-fold increase of progenitors was observed using a combination of IL-6 with SCF even when IL-6 concentrations greater than 50 ng/ml were used. These results demonstrated that sIL-6R is functional and capable of transducing proliferative signals in CD34$^+$ cells only in combination with IL-6. The results also indicate that 1280 μg/ml of sIL-6R and 50 ng/ml of IL-6 were the optimal concentrations for the expansion of progenitors in suspension culture with SCF.

To examine the effect of sIL-6R/IL-6 on the expansion of hematopoietic progenitor cells in more detail, both serum-containing and serum-free suspension cultures (supplemented with sIL-6R and IL-6 in combination with other factors) were carried out over a period of three weeks with a weekly analysis of progenitor cell expansion. FIG. 3 depicts the results of the generation of total progenitors from 2000 CD34$^+$ cells containing 684 progenitors in serum-containing suspension culture supplemented with single factors or combinations of factors at day 7 (open bars), day 14 (oblique bars) and day 21 (filled bars). The data are presented from a single experiment. Similar data were obtained in four additional experiments.

The number of progenitors found in cultures supplemented with IL-6 or sIL-6R alone gradually decreased, and nearly no progenitors remained to be found at day 14 or 21. Neither sIL-6R/IL-6 nor SCF alone had a significant affect on the expansion of progenitor cells. Cells supplemented with SCF and IL-6 increased in progenitor cell totals by 8.5-fold, 14-fold and 12-fold by days 7, 14 and 21, respectively. In contrast, the combination of sIL-6R, IL-6 and SCF dramatically increased the expansion of progenitor cells. Kinetic studies showed a continuous increase of total progenitor cells until day 14, followed by a decline until day 21. When compared with pre-expansion values, the overall increase in the progenitors was 44-fold, 61-fold and 33-fold by days 7, 14 and 21, respectively. About an 80-fold increase in the total of CD34$^+$ cells was observed at day 14 of culture by FACS analysis.

Weekly analyses of different subtypes of expanded progenitors in methylcellulose assay showed that all types of progenitors including GM colony-forming units (CFU-GM), erythroid burst-forming unit (BFU-E), CFU-Blast and CFU-Mix continued to be generated throughout the three weeks of culture in the presence of sIL-6R, IL-6 and SCF, although Mix colonies were barely detectable in other factor combinations. The number of CFU-Mix increased approximately 60-fold and 80-fold by days 7 and 14, respectively. Similar results were also obtained using serum-free suspension culture. Interestingly, considerable numbers of CFU-Mix, with a 40-fold increase, were obtained even at day 21 of serum-free suspension culture in the presence of sIL-6R, IL-6 and SCF.

These results revealed that sIL-6R/IL-6 acts synergistically with SCF in the expansion of hematopoietic progenitor cells. In subsequent experiments, sIL-6R/IL-6 was tested in combination with some early acting cytokines, including IL-3 and G-CSF, in the presence of SCF.

The study also compared the sIL-6R, IL-6 and SCF combination with an IL-3, IL-6 and SCF combination, which was the previous standard for use in expansion studies. The expansion of total progenitors using sIL-6R/IL-6/SCF was 1.5-fold of that resulting from the use of the IL-3, IL-6 and SCF combination.

The generation of CFU Mix with different cytokine combinations in both serum-containing and serum-free cultures is depicted in FIG. 4. The initial culture mixtures involved 2000 CD34$^+$ cells containing 786 progenitors and 188 CFU-Mix. The cultures were supplemented with various factor combinations in the presence of SCF at day 7 (open bars), day 14 (oblique bars) and day 21 (filled bars). The data are presented from a single experiment. Similar data were obtained in two additional experiments.

A combination of sIL-6, IL-6 and SCF expanded CFU-Mix by approximately 60-fold and 80-fold in serum-containing culture, by days 7 and 14, respectively, and by approximately 49-fold and 68-fold in serum-free culture, by days 7 and 14, respectively. Progenitor cells generated by a combination of IL-3, IL-6 and SCF were mainly of granulocyte and/or macrophage lineage, and CFU-Mix were only expanded about 30-fold in serum-containing and 10-fold in serum-free culture by day 14 of culture. The addition of IL-3 to the combination of sIL-6R, IL-6 and SCF did not increase the expansion of CFU-Mix. Intriguingly, the addition of G-CSF to the combination appeared to have negative effects on the expansion. These results demonstrated that the combination of sIL-6R, IL-6 and SCF is a more potent expansion combination, especially for the expansion of primitive progenitors.

Example 3

The Effects of Anti-gp130 mAb and Anti-IL-6R mAb on the Expansion of Multipotential Cells To verify the involvement of gp130 in the sIL-6R/IL-6 complex-mediated hematopoietic progenitor cell expansion, the affects of mouse anti-human gp130 mAbs and anti-human IL-6R mAb on progenitor cell expansion were evaluated.

Preparation of Antibodies. The preparation of anti-human gp130 monoclonal antibodies (such as, GPX7, GPX22 and GPZ35) is known (2,19). These three mAbs recognize different epitopes on the gp130 receptor and are known to inhibit IL-6-mediated biological response through the inhibition of the IL-6 induced association of the gp130 and IL-6 receptors. Anti-human IL-6R mAb (PM1) was also prepared (20). PM1 is known to inhibit IL-6-mediated biological response through the inhibition of the binding of IL-6R to IL-6.

It was found that the addition of anti-gp130 mAbs dose-dependently inhibited the expansion of total progenitor cells in the serum-containing suspension culture. FIG. 5 illustrates the resulting expansion of total progenitor cells (○) and CFU-Mix (•) in cultures containing a combination of sIL-6R, IL-6 and SCF, and of total progenitor cells in cultures containing a combination of IL-3 and SCF (Δ), when varying concentrations of anti-human gp130 mAbs (A) and anti-human IL-6R mAb (B) are added to the cultures. The cultures without mAbs were estimated as control experiments. The data present the ratio of the progenitor cells generated in each culture treated with mAbs to those obtained with control, and are expressed as a percent (%) of control.

The expansion of CFU-Mix was completely blocked at an anti-gp130 mAb concentration of 1 μg/ml, whereas the mAbs appeared to have little or no effect on the expansion induced by the combination of IL-3 and SCF. The addition of anti-IL-6R mAb to cultures caused a similar display of inhibition, except at a slightly lower efficiency, with the complete abrogation of CFU-Mix expansion observed at a concentration of 10 μg/ml (FIG. 5B). The anti-IL-6R antibody also failed to affect expansion stimulated by the combination of IL-3 and SCF. In contrast, an anti-EPO antibody inhibited the expansion induced by SCF and EPO but had no effect on that induced by sIL-6R, IL-6 and SCF (data not shown). The same results were obtained in both serum-free suspension culture and methylcellulose culture.

Erythroid Cell Production

Studies were also performed to further examine the effects of gp130 signaling on the generation of erythroid cells from human hematopoietic progenitor cells. Normal human hematopoietic progenitor/stem cells were isolated from cord blood mononuclear cells and were cultured in the presence of varying concentrations of sIL-6R together with IL-6 and SCF. It was found that the total cell numbers increased in a dose-dependent manner. This increase was detectable with sIL-6R at a concentration as low as 80 ng/ml and appeared to plateau at 1280 ng/ml. FIG. 6 depicts the results of one experiment using varying amounts of sIL-6R in the presence of IL-6 and SCF.

The analyses of total cell numbers indicated more than 30-fold, 650-fold and 900-fold expansions of total cells in cultures at 7, 14 and 21 days of incubation, respectively, at the sIL-6R concentrations exceeding 1280 ng/ml. In the absence of IL-6, however, sIL-6R failed to increase the total cell number. These results clearly indicated that sIL-6R is functional and capable of transducing proliferative signals in CD34$^+$ cells only in combination with IL-6.

Figure 7:
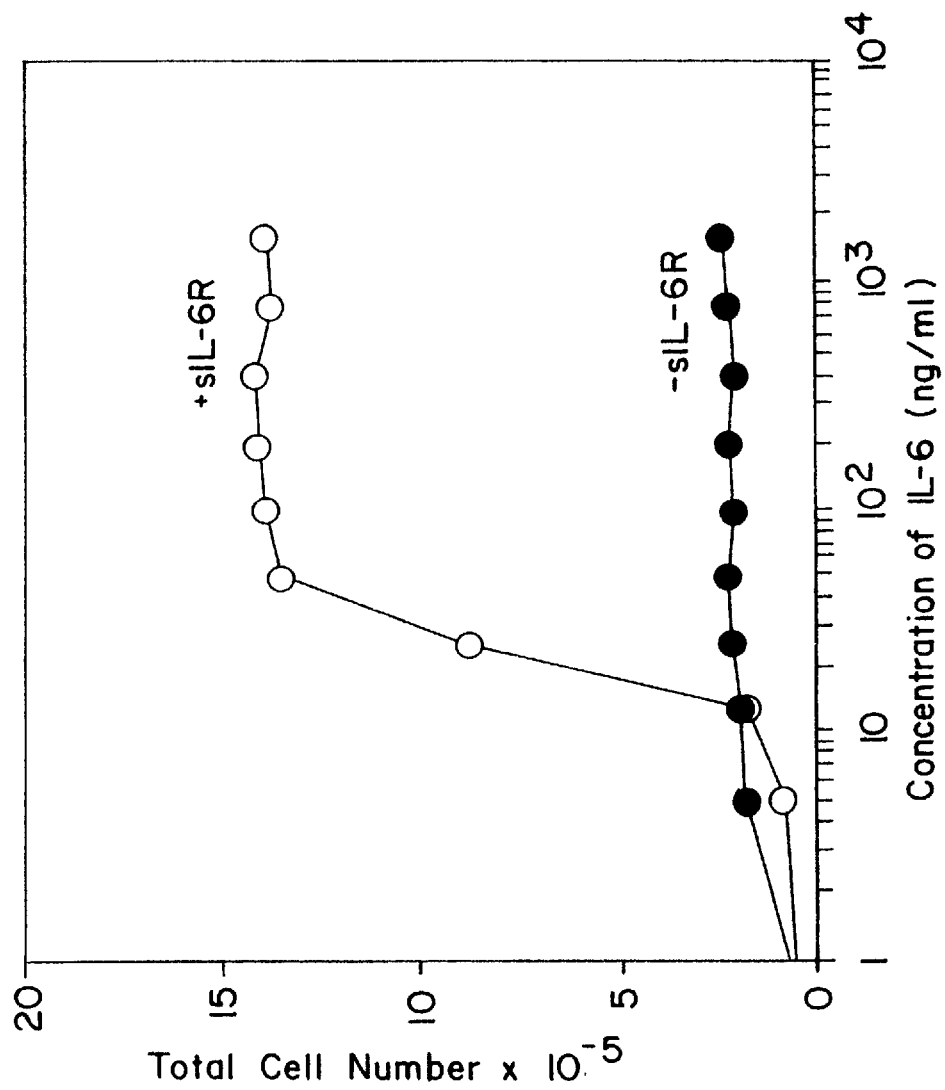
FIG. 7 the effects of varying amounts of IL-6 in the presence of sIL-6R and SCF.

Dose response studies of IL-6 also indicated a dose-dependent increase in the total cell numbers. A maximal cell number was obtained using IL-6 concentrations of 50–100 ng/ml in the presence of 1280 ng/ml sIL-6R (FIG. 7). In the absence of sIL-6R, however, IL-6 generated only a small increase in the number of total cells, even when used in amounts greater than 50 ng/ml. These results suggest that sIL-6R at 1280 ng/ml and IL-6 at 50 ng/ml may be an effective combination for the expansion of total cells from purified stem cells in serum-containing culture with SCF. The expansion of total cells by the combination of sIL-6R, IL-6 and SCF was also observed when CD34$^+$ cells purified from human bone marrow were used (data not shown).

Figure 8:
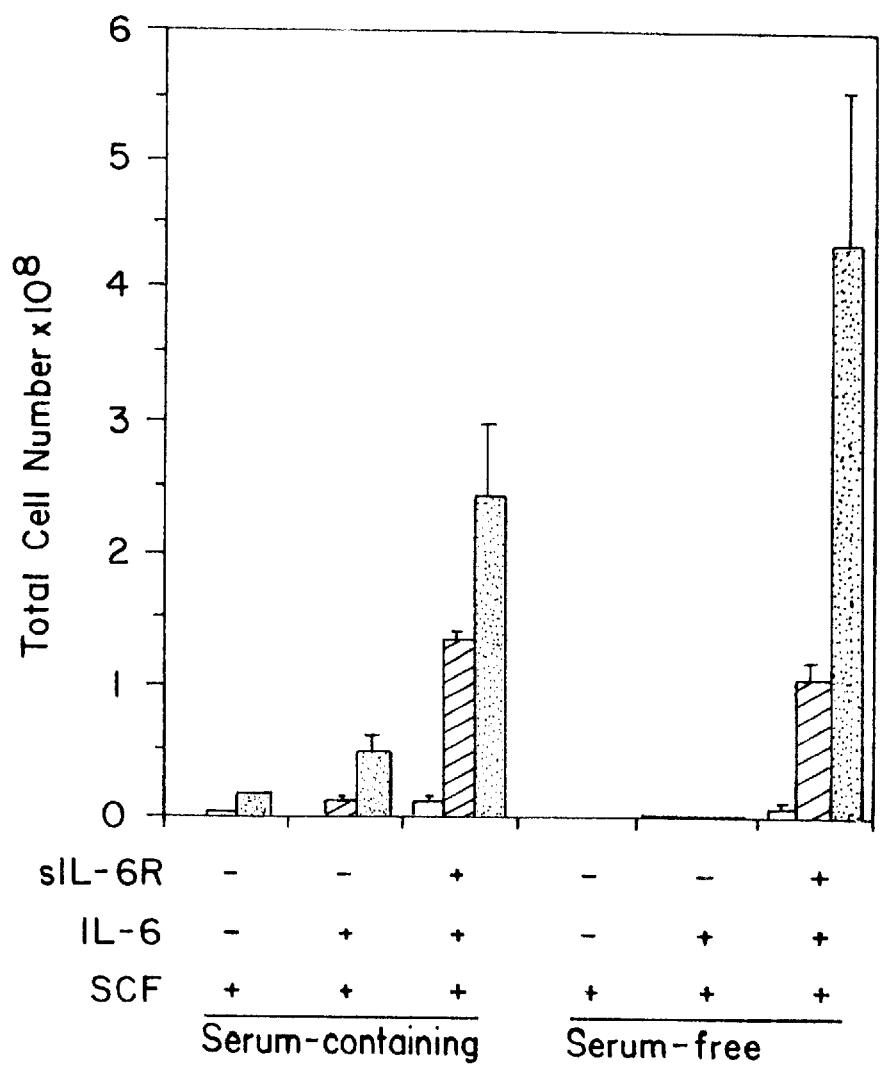
FIG. 8 illustrates the effects of SCF, IL-6/SCF and sIL-6R/IL-6/SCF on serum-free and serum-containing cultures.

It was possible that the observed effects of combined sIL-6R/IL-6 in serum-containing culture were due to the actions of these factors in conjunction with unknown factor(s) contaminating the fetal bovine serum (FBS), rather than to the sIL-6R/IL-6/SCF combination alone. To exclude this possibility, a serum-free suspension culture of CD34$^+$ cord blood cells was studied. Surprisingly, an even greater synergy between sIL-6R, IL-6 and SCF, was observed in the serum-free cultures as compared to the serum-containing cultures (FIG. 8). Serum-free culture of cells with the combination of sIL-6R, IL-6 and SCF promoted 38-fold, 530-fold and 2200-fold expansions of total cell numbers at 7, 14 and 21 days of culture, respectively. Cells cultured in SCF alone, or in combination with IL-6, demonstrated only a 2.2 or 7.5-fold expansion even at day 21. These results clearly excluded the possible influence of unknown factors and demonstrated that sIL-6R in the presence of SCF does induce the expansion of hematopoietic stem cells.

Cytocentrifuge preparations of expanded cells were stained with various cytochemical and immunological stains. Differential cell counts of these cells indicated the presence of mainly blast cells, such as those presented at day 7 of culture of CD34$^+$ cord blood cells (FIG. 9a). Interestingly, a number of erythroblasts were observed in both serum-containing and serum-free suspension cultures, at day 14 of culture, when using the combination of sIL-6R, IL-6 and SCF. The nature of the erythroid cells was confirmed by benzidine-staining and immunostaining with monoclonal antibodies against glycophorin A (FIG. 9b) and hemoglobin-a (FIG. 9c). Some of the erythroid cells differentiated to the normoblast and enucleated erythrocyte stages (FIG. 9d). At 21 days of culture, most of the erythroid cells differentiated to the normoblast stage, and many enucleated erythrocytes were observed.

The absolute number of erythroid cells was calculated by total cell number and the occurrence of glycophorin A-positive cells on the cytospine slides. Weekly analyses of the absolute number of erythroid cells in serum-free cultures receiving various combinations of cytokines and sIL-6R are presented in FIG. 10.

The combination of sIL-6R, IL-6 and SCF stimulated the generation of not only total cell number but also total erythroid cells more significantly than did other combinations. At two weeks of culture, approximately 79% of the cells generated by the combination were erythroid cells (i.e., E-blasts and erythrocytes). At three weeks of culture, approximately 69% of the cells generated by the combination were erythroid cells. A small number of erythroid cells was also observed in cultures containing sIL-6R and IL-6 in combination with either IL-3 or GM-CSF, suggesting that gp130 signaling plays a role in the generation of erythroid cells in vitro.

No erythroid cells were detectable in cultures receiving other cytokine combinations, except those combinations which included erythropoietin. In comparison to erythropoietin alone, the total number of erythroid cells produced by the combination of sIL-6R, IL-6 and SCF was about 5-fold at 14 days of culture, and about 115-fold at 21 days of culture (FIG. 10). In comparison to a combination of erythropoietin, sIL-6R and IL-6, the total number of erythroid cells produced by the sIL-6R/IL-6/SCF combination was about 4.1-fold at 14 days of culture, and about 38.3-fold at 21 days of culture. The effect of the sIL-6R/IL-6/SCF combination on the generation of erythroid cells was observed in both serum-containing and serum-free culture of CD34$^+$ bone marrow cells (data not shown).

In the suspension cultures receiving the sIL-6R/IL-6/SCF combination, it was likely that the generation of the large number of erythroid cells resulted from the proliferation, differentiation and maturation of immature erythroid progenitors in the CD34$^+$ cell population. To confirm this possibility, methylcellulose clonal cultures of CD34$^+$ cells were studied. Cultures received either erythropoietin alone, combined erythropoietin/IL-6 or an erythropoietin/sIL-6R/IL-6 combination. Table 1 depicts the results produced from 500 CD34$^+$ cord blood cells cultured for 14 days.

TABLE 1

|  | Erythroid Bursts | Mixed Erythroid Colonies |
| --- | --- | --- |
| EPO | 57.7 ± 14.8 | 0 |
| EPO/IL-6 | 63.0 ± 3.5 | 0 |
| EPO/sIL-6R/IL-6 | 65.0 ± 7.6 | 9 ± 6.1 |

The combination of sIL-6R, IL-6 and SCF, in the absence of erythropoietin, stimulated not only erythroid bursts, but also generated many large mixed erythroid colonies. All of the mixed erythroid colonies contained many mature erythroid cells, including erythrocytes (FIG. 9f and FIG. 9g). The sIL-6R/IL-6/SCF combination produced 27.2±5.8 erythroid bursts and 122.3±21.8 mixed erythroid colonies from the 500 CD34$^+$ cord blood cells. In contrast, neither erythroid bursts nor mixed erythroid colonies were observed in cultures receiving SCF alone or SCF in combination with IL-6. The generation of erythroid bursts and mixed erythroid colonies from both cord blood and bone marrow stem cells using the sIL-6R/IL-6/SCF combination was also confirmed in serum-free cultures (data not shown). When bone marrow mononuclear cells which contain mature erythroid progenitors (i.e., colony forming unit-erythroid) were cultured with the sIL-6R/IL-6/SCF combination, a number of erythroid colonies were observed. These results strongly suggested that the sIL-6R/IL-6/SCF combination can support proliferation, differentiation and terminal maturation not only of immature erythroid progenitors in the CD34$^+$ cell population but also mature erythroid progenitors in bone marrow mononuclear cells.

Figure 11:
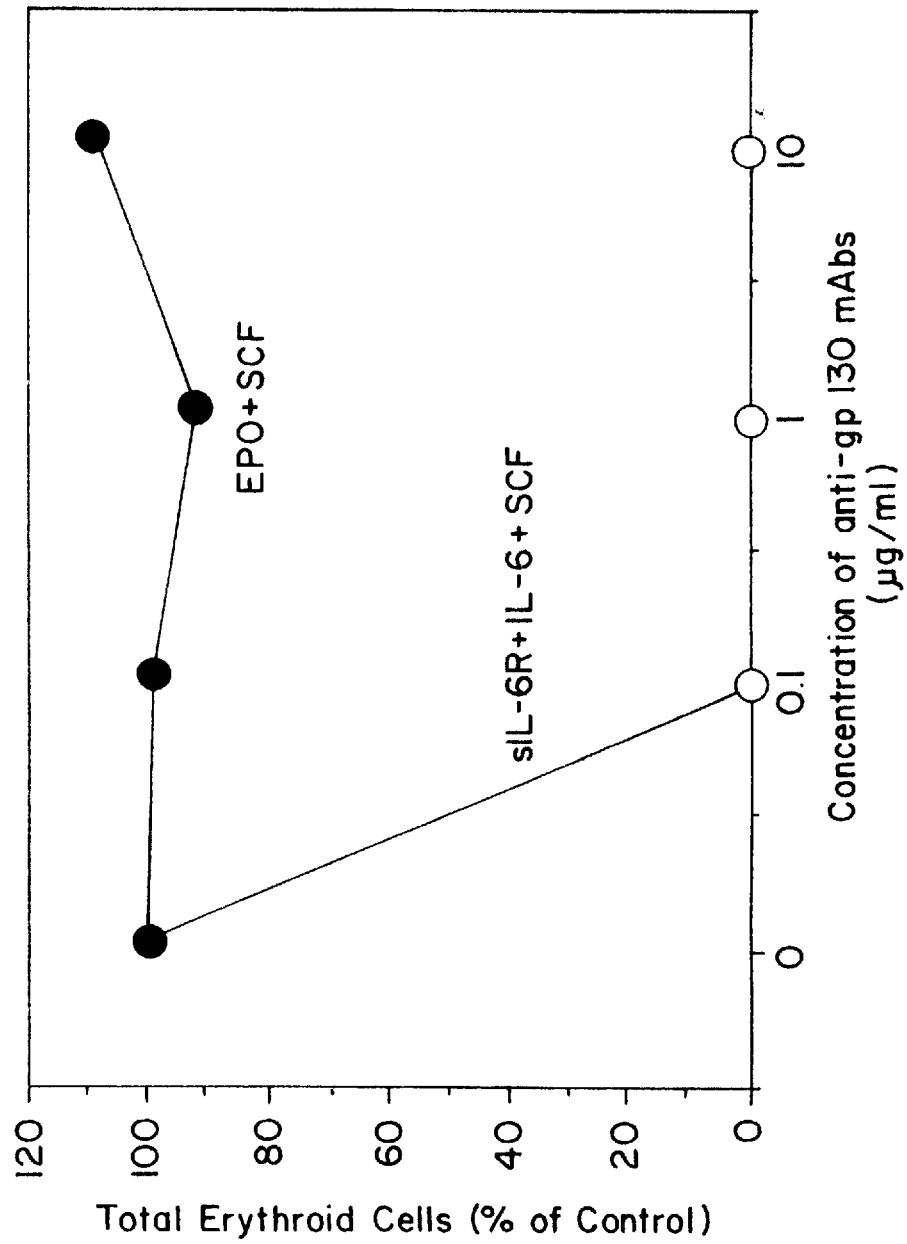
FIG. 11 depicts the effects of anti-gp130 MAbs ($\mu$g/ml) on suspension cultures receiving a combination of sIL-6R/IL-6/SCF or EPO/SCF.

To further test the possibility of an alternative pathway for the regulation of erythropoiesis, we examined the effects of different antibodies on cell development. The effects of the following antibodies were studied: anti-gp130 MAbs (GPX7, GPX22 and GPZ35) which block the interaction between sIL-6R/IL-6 complex and cell-surface gp130 (19, 29); anti-IL-6R MAb which blocks the interaction between IL-6 and IL-6R (20); and anti-erythropoietin neutralizing antibody which blocks the development of erythroid cells from CD34$^+$ cells. The addition of anti-gp130 MAbs to the suspension culture receiving the sIL-6R/IL-6/SCF combination completely abrogated the production of erythroid cells (FIG. 11). The anti-gp130 antibodies, however, had no effect on the erythropoietin-dependent production of erythroid cells.

Figure 12:
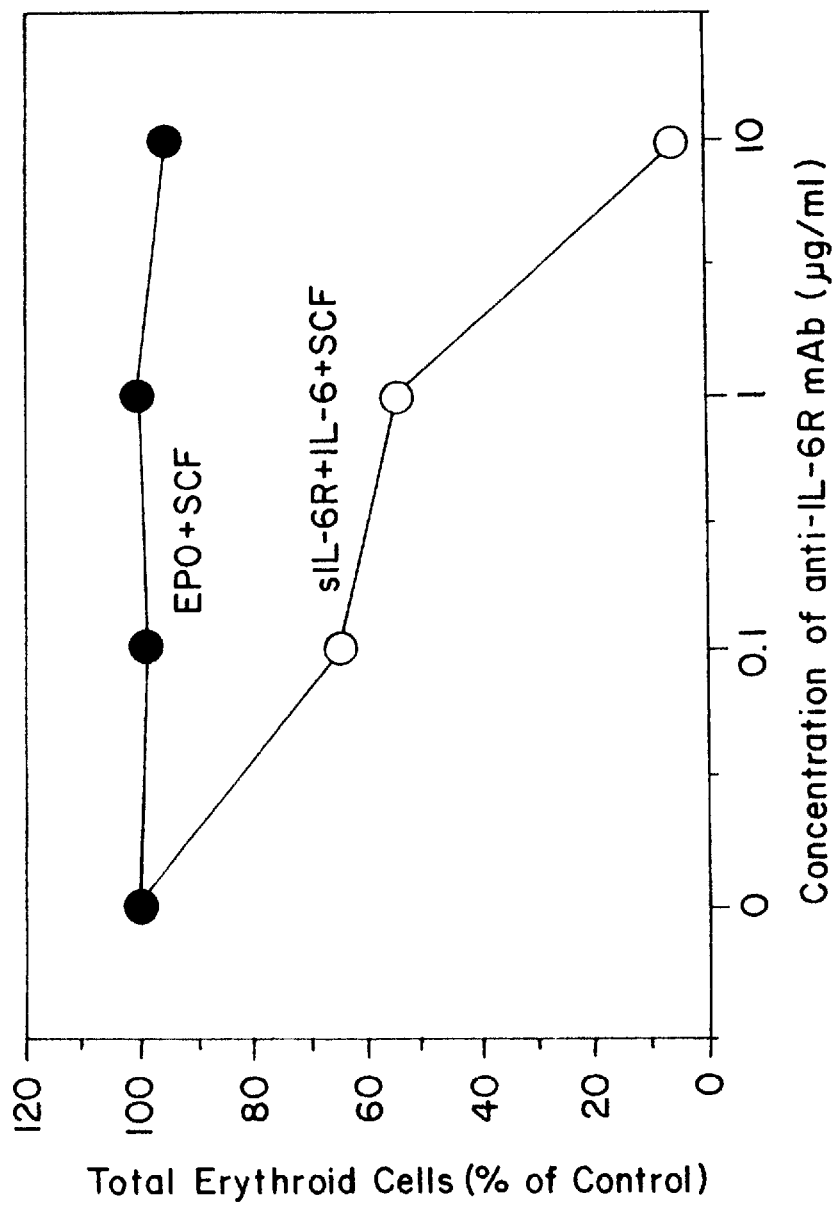
FIG. 12 depicts the effects of an anti-IL-6R MAb ($\mu$g/ml) on suspension cultures receiving a combination of sIL-6R/IL-6/SCF or EPO/SCF.
Figure 13:
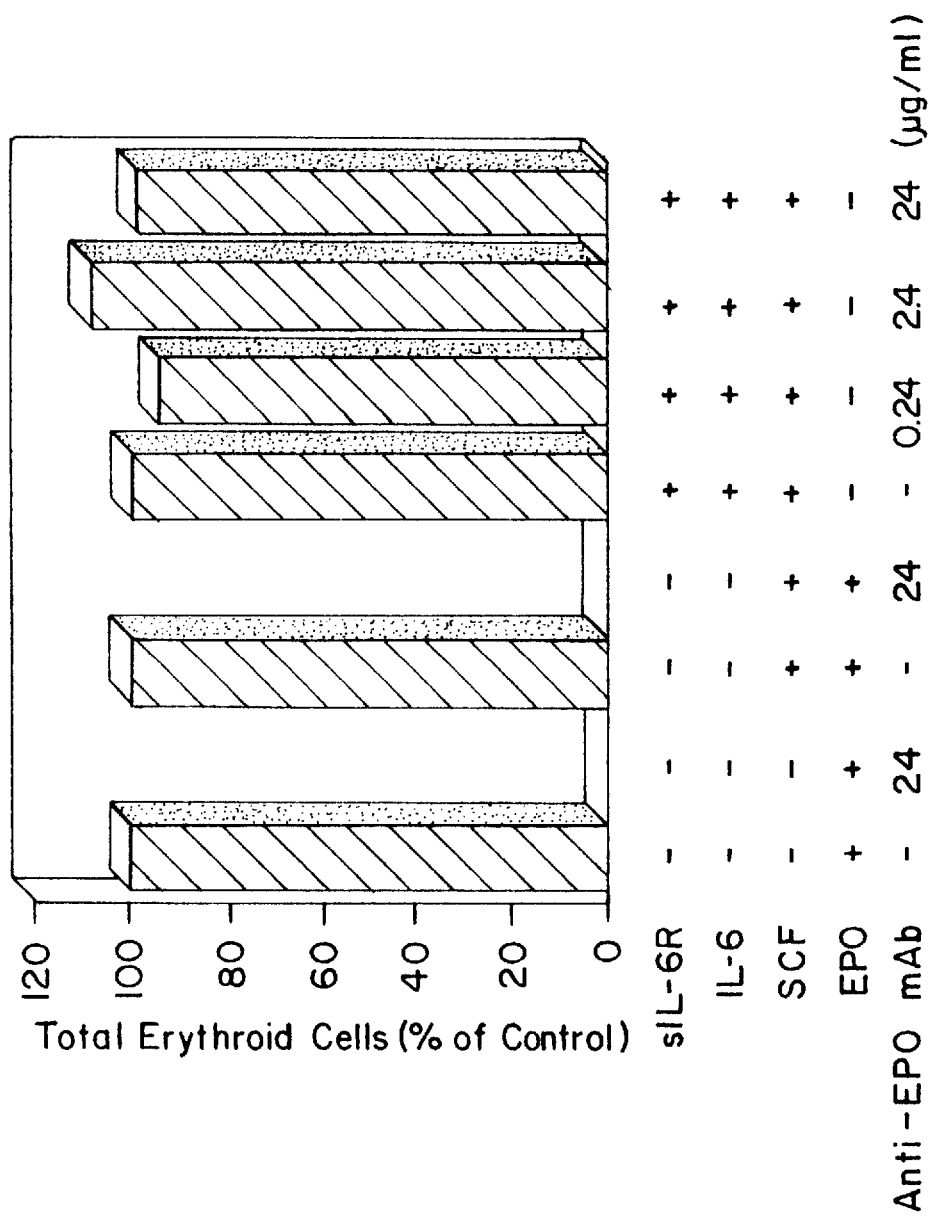
FIG. 13 depicts the effects of an anti-EPO antibody ($\mu$g/ml) on suspension cultures receiving EPO, EPO/SCF or a combination of sIL-6R/IL-6/SCF.

The addition of the anti-IL-6R MAb, at a concentration of 10 mg/ml, to cultures receiving the sIL-6R/IL-6/SCF combination resulted in almost complete inhibition of erythroid cell production (FIG. 12). The lower efficiency of the anti-IL-6R MAb may be explained by the excess of sIL-6R which may interfere with the antibody neutralization of the interaction between IL-6 and the cell surface IL-6R. In contrast, although an anti-erythropoietin antibody almost completely inhibited erythropoietin-dependent production of erythroid cells, it failed to affect the generation of erythroid cells by the sIL-6R/IL-6/SCF combination (FIG. 13).

Methylcellulose clonal culture of hematopoietic stem cells also indicated that the anti-gp130 MAbs, but not the anti-erythropoietin antibody, completely blocked the development of both erythroid burst and mixed erythroid colony formation which was otherwise induced by the sIL-6R/IL-6/SCF combination. These results clearly demonstrate that the observed effects of the interleukin-6 ligand and soluble receptor result from the interaction of IL-6 and sIL-6R, and the association of the resulting IL-6/sIL-6R complex with membrane-anchored gp130 on the target progenitor cells. The results also indicated that the generation of erythroid cells from immature erythroid progenitors by gp130 signaling in combination with SCF occurs independently from the presence of erythropoietin.

It has been believed that the proliferation and terminal maturation of erythroid cells are regulated physiologically by erythropoietin receptor signaling. The present invention demonstrates that gp130 signaling combined with SCF will stimulate immature erythroid progenitors, giving rise to erythroblasts and erythrocytes in the absence of erythropoietin. This in turn suggests that erythropoietin receptor signaling is not obligatory for proliferation, differentiation and terminal maturation of normal human erythroid cells. The significant production of erythroid cells by the sIL-6R/IL-6/SCF combination, and the lack of such production by stem cells which did not receive sIL-6R, is reminiscent of previous reports that sIL-6R confers IL-6 responsiveness to cells which lack transmembrane IL-6R but which express gp130. This theory was supported by the immunocytological staining experiments which demonstrated that all CD34$^+$ cells and proliferating cells expressed gp130, but about 90% of the CD34$^+$ cells receiving the sIL-6R/IL-6/SCF combination were negative for IL-6R staining.

It has been reported that the physiological significance of sIL-6R is indicated by its detection in human sera (26). The sIL-6R present in sera is biologically active in terms of its ability to bind IL-6 and eventually to stimulate gp130 (30). A half-maximal effect of the combination of sIL-6R and IL-6 on the generation of erythroid cells from CD34$^+$ cells in vitro was observed at concentrations of 320 ng/ml of sIL-6R and 25 ng/ml of IL-6. This seems likely to be within the physiological range. IL-6 and SCF are also detectable in human sera. Like IL-6, both soluble and membrane-bound forms of SCF are produced by bone marrow stroma cells which may anchor hematopoietic stem cells and immature progenitors and support their proliferation in bone marrow (27,28,31,32). Taken together, the current results indicate that SCF, in combination with gp130 signaling, plays an important role on normal erythropoiesis in vivo.

Example 4

Proliferative Activity of sIL-6R and IL-6 on Human Hematopoietic Stem Cells

METHODS. Human umbilical cord blood, obtained according to institutional guidelines, was collected during normal full-term deliveries. Mononuclear cells were separated by Ficoll-Hypaque density gradient centrifugation after depletion of phagocytes with Silica (IBL, Fujioka, Japan). After washing, the mononuclear cells were mixed with magnetic particles bearing anti-CD34 antibody (Dynabeads M-450 CD34; Dynal, Oslo, Norway), with a bead to cell ratio of 1:1. The cell-bead suspension was suspended and incubated at 4° C. for 30 minutes to allow cell binding to the beads. The resulting beads/rosetted cells were collected in a Dynal Magnetic Particle Concentrator. The beads were detached from the positively selected cells by DETACHaBead CD34 (Dynal), according to the manufacturer's instructions, to retrieve the selected CD34$^+$ cells. The purity of the separated CD34$^+$ cells was 85–95% by FACS analysis (Ortho, USA).

Colony efficiency in methylcellulose culture, supplemented with SCF, IL-3, IL-6, erythropoietin and G-CSF, was 45–55%. Purified CD34$^+$ cells were cultured in suspension culture using the techniques previously described (21,22) with the following modifications. Culture medium contained 2000 CD34$^+$ cells, a-medium, 20% fetal bovine serum (FBS; HyClone, Utah), 1% crystallized and deionized bovine serum albumin (BSA, Sigma). One milliliter of culture mixture and different combinations of recombinant human sIL-6R, IL-6, and SCF (100 ng/ml) were incubated in 24-well tissue plates (Nunc, Kamstrup, Denmark) at 37° C. with 5% $CO_2$ and 5% $O_2$. Recombinant sIL-6R, IL-6 and SCF were produced and used as previously described. Serum-free suspension cultures consisted of 2% pure BSA (Sigma), 10 mg/ml insulin, 200 mg/ml transferrin, $10^{-5}$M mercaptoethanol (Eastman) and 40 mg/ml low-density lipoprotein (Nakarai Tesque Inc., Tokyo), instead of FBS (10). At weekly intervals, half of the medium was exchanged with fresh medium containing the same set of cytokines. A fraction of the cells was then harvested, washed, counted in a hemocytometer, cytocentrifuged and stained.

RESULTS. The results of the study are presented in FIGS. 10 through 12, as discussed above. FIG. 10 depicts stem cell growth, in serum-containing suspension culture, using varying concentrations of sIL-6R with SCF in the presence (○) or absence (•) of IL-6 (50 ng/ml) at 14 days of incubation. FIG. 11 depicts stem cell growth, in serum-containing suspension culture, using varying concentrations of IL-6 with SCF in the presence (○) or absence (•) of sIL-6R (1280 ng/ml) at 14 days of incubation. FIG. 12 depicts stem cell growth in serum-containing and serum-free cultures containing either SCF alone, a combination of SCF and IL-6 (50 ng/ml) or a combination of SCF/IL-6 and sIL-6R (1280 ng/ml) at day 7 (open columns), day 14 (oblique columns) and day 21 (filled columns). The results are from three separate experiments. Standard deviations are represented by error bars.

Example 5

Development of Erythroid Cells from Hematopoietic Stem Cells in Culture with Combined Cytokines METHODS. Cytocentrifuge preparations of suspension culture were stained with May-Grunwald-Giemsa at day 7 and day 14 by conventional methods. At day 14, preparations were also immunostained with the alkaline phosphatase anti alkaline phosphatase (APAAP) method using MAbs against antiglycophorin A (Immunotech Co, Marseilles, France) and anti hemoglobin α-chain (COSMO Bio Co., Tokyo, Japan) according to previously described methods (23). Positive cells were stained with reddish granules. Methylcellulose culture was conducted as previously reported (23,24). Culture mixture contained 500 CD34$^+$ cord blood cells, a-medium, 0.9%, 30% FBS, 1% BSA, $5\times10^{-5}$M mercaptoethanol, 1280 ng/ml sIL-6R, 80 ng/ml IL-6 and 100 ng/ml SCF. One milliliter of culture mixture was plated in each 35 mm Lux standard nontissue culture dish. Cells were incubated at 37° C. in a humidified atmosphere with 5% $CO_2$ in air.

RESULTS. The results of the study are presented in FIG. 9. Cytocentrifuge preparations of suspension culture stained with May-Grunwald-Giemsa are depicted at day 7 (FIG. 9a) and day 14 (FIG. 8d). Cytocentrifuge preparations of the culture immunostained with antiglycophorin-A MAb or anti hemoglobin-alpha MAb at day 14 are depicted in FIGS. 9b and 9c, respectively. Representative erythroid burst and mixed erythroid colony generated from erythroid progenitor cells in methylcellulose culture with sIL-6R, IL-6 and SCF at day 14 are depicted in FIGS. 9e and 9f, respectively.

Example 6

Antibody Effects on Erythroid Cell Production

METHODS. The following experiment examined the effects of anti-human gp130 MAbs, anti-human IL-6R MAb and anti-human erythropoietin antibody on the generation of erythroid cells. The preparation of anti-human gp130 MAbs (GPX7, GPX22 and GPZ35) has been described previously (2). In brief, mice were immunized with recombinant human soluble gp130, and hybridomas producing the anti-human gp130 MAbs GPX7, GPX22 and GPZ35 were established. The three antibodies recognize different epitopes on gp130 and inhibit IL-6-mediated biological response through the inhibition of the IL-6-induced association of gp130 with IL-6 receptors (2,19). Anti-human IL-6R (PM1) MAb was prepared (20). PM1 inhibits IL-6-mediated biological response through inhibition of the binding of IL-6 to the IL-6 receptors. Rabbit anti-human erythropoietin antibody (IgG K-5) was provided by Kirin Co., Japan. Anti-erythropoietin antibody (24 mg/ml) neutralizes 2U/ml of erythropoietin (34).

As illustrated in FIG. 11, human cord blood stem cells (2000 CD34$^+$ cells) were supplemented with either a combination of sIL-6R/IL-6/SCF (○) at the predetermined optimal concentrations, or a combination of erythropoietin (2U/ml) and SCF (100 ng/ml) (•). Cultures were observed with and without the addition of mouse anti-human gp130 MAbs (FIG. 11), mouse anti-human IL-6R MAb (PM1) (FIG. 12) or rabbit anti-human erythropoietin antibody (FIG. 13) in serum-containing suspension culture, made as described in Example 4. Graded concentrations of the antibodies were added at the beginning of the culture. The wells to which no antibodies were added were used as controls. After culturing for 14 days, the cells were harvested, counted and cytocentrifuged. Total erythroid cells (including erythroblasts, normoblasts and erythrocytes) were calculated based on the total cell number and the proportion of the erythroid cells determined on the cytospin slides. The resulting data represent the ratio of the erythroid cells in each well treated with antibodies to the erythroid cells in each control well, and are expressed as a percent (%) of control.

References

1. Kishimoto et al, Science, 258:593–597 (1992).
2. Taga et al, Proc. Natl. Acad. Sci., USA, 89:10998–11001 (1992).
3. Murakami et al, Science, 260:1808–1810 (1993).

4. Kishimoto et al, *Cell,* 76:253–262 (1994).
5. Hibi et al, *Cell,* 63:1149–1157 (1990).
6. Mackiewicz et al, *J. Immunol.,* 149:2021–2027 (1992).
7. Yasukawa et al, *Immunol. Lett.,* 31:123–130 (1992).
8. Saito et al, *Immunol.,* 148:4066–4071 (1992).
9. Ikebuchi et al, *Proc. Natl. Acad. Sci., USA,* 84:9035–9039 (1987).
10. Koike et al, *Exp. Med.,* 168:879–890 (1988).
11. Tanaka et al, *Blood,* 80:1743–1749 (1992).
12. Haylock et al, *Blood,* 80:1405–1412 (1992).
13. Sato et al, *Blood,* 82:3600–3609 (1993).
14. Koller et al, *Blood,* 82:378–384 (1993).
15. Brugger et al, *Blood,* 81:2579–2584 (1993).
16. Yoshida et al, *Mech. Dev.,* 45:163–171 (1994).
17. Yasukawa et al, *J. Biochem.,* 108:673–676 (1990).
18. Taga et al, *Cell,* 58:573–581 (1989).
19. Saito et al, *J. Immunol. Methods,* 163:217–233 (1993).
20. Hirata et al, *J. Immunol.,* 143:2900–2906 (1989).
21. Iscove et al, *J. Immunol.,* 142:2331–2337 (1989).
22. Mayani et al, *Blood,* 83:2410–2417 (1994).
23. Nakahata et al, *J. Clin. Invest.,* 70:1324–1328 (1982).
24. Imai et al, *Blood,* 78:1969–1974 (1991).
25. Tamura et al, *Proc. Natl. Acad. Sci., USA,* 90:1924–1928 (1993).
26. Honda et al, *J. Immunol.,* 148:2175–2180 (1992).
27. Honda et al, *J. Immunol.,* 145:4059–4064 (1990).
28. Langley et al, *Blood,* 81:656–660 (1993).
29. Yin et al, *J. Immunol.,* 151:2555–2561 (1993).
30. Suzuki et al, *Eur. J. Immunol.,* 23:1078–1082 (1993).
31. Zsebo et al, *Cell,* 63:213–224 (1990).
32. Flanagan et al, *Cell,* 63:185–194 (1990).
33. Okumura et al, *Blood,* 80:642–650 (1992).
34. Nishi et al, *Blood,* 76:1330–1335 (1990).

What is claimed is:

1. A method for the ex vivo expansion of multipotential hematopoietic cells, comprising culturing the cells in a medium comprising soluble interleukin-6 receptor, interleukin-6, and stem cell factor, said cells, interleukin-6 receptor, interleukin-6, and stem cell factor derived from a human species, said interleukin-r receptor, interleukin-6, and stem cell factor being present in amounts effective to produce a mature erythroid cell population in the absence of erythropoietin.

2. The method according to claim 1, wherein the cells to be expanded are obtained from cord blood, peripheral blood or bone marrow.

3. The method according to claim 1, wherein the multi-potential hematopoietic cells are progenitor and/or stem cells obtained by CD34 selection.

4. The method according to claim 1, wherein the multi-potential hematopoietic cells are stem cells functionally selected by the removal of proliferating cells.

5. The method according to claim 1, wherein said soluble interleukin-6 receptor is used at a concentration of at least 80 ng/ml to 1280 ng/ml.

6. The method according to claim 5, wherein said interleukin-6 is used at a concentration of at least 50 ng/ml to 100 ng/ml.

7. A kit, consisting of: soluble interleukin-6 receptor, interleukin-6 and stem cell factor, said soluble interleukin-6 receptor, interleukin-6 and stem cell factor provided in individual containers or as a mixture in a single container in an amount effective for use in expansion of multipotential hematopoietic cells according to claim 1.

8. A method generating differentiated blood cell colonies by ex vivo expansion of multipotential hematopoietic cells, comprising culturing the hematopoietic cells in a medium comprising soluble interleukin-6 receptor, interleukin-6, and stem cell factor, said hematopoietic cells, interleukin-6 receptor, interleukin-6, and stem cell factor derived from a human species, said interleukin-6 recaptor, interleukin-6, and stem cell factor being present in amounts effective to produce a mature erythroid cell population in the absence of erythropoietin.

* * * * *

UNITED STATES PATENT AND TRADEMARK OFFICE
CERTIFICATE OF CORRECTION

PATENT NO.   : 5,861,315

DATED        : January 19, 1999

INVENTOR     : Tatsutoshi Nakahata

It is certified that error appears in the above-identified patent and that said Letters Patent is hereby corrected as shown below:

Column 1, line 37, change "(3CF)" to -- (SCF) --.

Signed and Sealed this

Twenty-fifth Day of May, 1999

Attest:

Q. TODD DICKINSON

*Attesting Officer*     *Acting Commissioner of Patents and Trademarks*